(12) United States Patent
Maeda et al.

(10) Patent No.: US 7,192,682 B2
(45) Date of Patent: Mar. 20, 2007

(54) UNSATURATED MONOMERS, POLYMERS, CHEMICALLY-AMPLIFIED RESIST COMPOSITION, AND PROCESS OF PATTERN FORMATION

(75) Inventors: Katsumi Maeda, Tokyo (JP); Kaichiro Nakano, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 10/497,302

(22) PCT Filed: Jun. 27, 2003

(86) PCT No.: PCT/JP03/08209

§ 371 (c)(1),
(2), (4) Date: Jun. 1, 2004

(87) PCT Pub. No.: WO2004/003035

PCT Pub. Date: Jan. 8, 2004

(65) Prior Publication Data
US 2004/0265732 A1 Dec. 30, 2004

(30) Foreign Application Priority Data
Jun. 28, 2002 (JP) ............................. 2002-190827

(51) Int. Cl.
G03F 7/039 (2006.01)
G03F 7/30 (2006.01)
G03F 7/38 (2006.01)
C08F 10/00 (2006.01)
C08F 136/00 (2006.01)

(52) U.S. Cl. ................... 430/270.1; 430/326; 430/905; 430/910; 526/281; 526/282; 549/30; 549/298

(58) Field of Classification Search ............. 430/270.1, 430/326, 905, 910; 526/281, 282; 549/298, 549/30, 300
See application file for complete search history.

(56) References Cited

U.S. PATENT DOCUMENTS

2003/0008232 A1* 1/2003 Kinsho et al. ........... 430/270.1
2004/0110085 A1* 6/2004 Iwai et al. ............... 430/270.1

FOREIGN PATENT DOCUMENTS

| JP | 59-45439 | 3/1984 |
| JP | 2856116 | 11/1998 |
| JP | 2964990 | 8/1999 |
| JP | 2000-159758 | 6/2000 |
| JP | 2001-233917 | 8/2001 |
| JP | 2001-242627 | 9/2001 |
| JP | 2001-294570 | 10/2001 |
| JP | 2001-296661 | 10/2001 |
| JP | 2001-354669 | 12/2001 |

(Continued)

OTHER PUBLICATIONS

Japan Chemistry Academy Basic II, 3rd edition, 1984, pp. 502-504.
Mathew et al., "(n³-Allyl)palladium(II) and Palladium (II) Nitrile Catalysts for the Addition Polymerization of Norbornene Derivatives with Functional Groups", Macromolecules, 1996, 29, pp. 2755-2763.
Chiba et al., "157 nm Resist Materials: A Progress Report", Journal of Photopolymer Science and Technology, 2000, vol. 13, No. 4, pp. 657-664.
Tabushi et al., "Regio- and Stereospecific [2π +2o +2o] Cycloaddition Reaction of Quadricyclane", J. Am. Chem. Soc., 1971, vol. 94, pp. 787-792.

(Continued)

Primary Examiner—Richard L. Schilling
(74) Attorney, Agent, or Firm—Young & Thompson

(57) ABSTRACT

There is provided a chemically-amplified resist composition having high transparency to light having a wavelength of 220 nanometers or smaller, excellent resistance to etching, and excellent adhesion to a substrate. The chemically-amplified resist composition is prepared through the use of at least one of a repeated structural unit having a bridged alicyclic γ-lactone structure defined in the general formula (III), a repeated structural unit having a bridged alicyclic γ-lactone structure defined in the general formula (IV), and a repeated structural unit having a bridged alicyclic γ-lactone structure defined in the general formula (V).

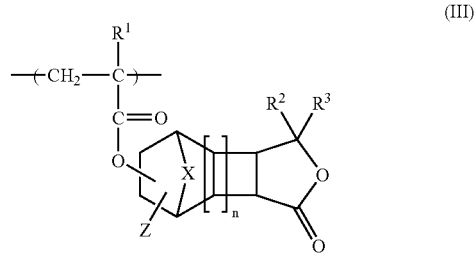

(III)

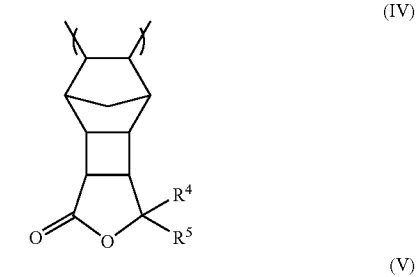

(IV)

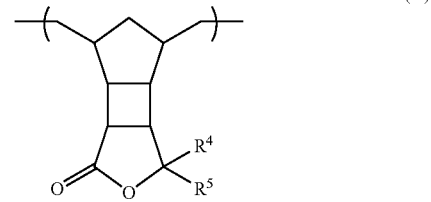

(V)

9 Claims, No Drawings

FOREIGN PATENT DOCUMENTS

| | | |
|---|---|---|
| JP | 2001-354756 | 12/2001 |
| JP | 2002-20426 | 1/2002 |
| JP | 2002-53571 | 2/2002 |
| JP | 2002-308866 | 10/2002 |
| JP | 2002-371114 | 12/2002 |

OTHER PUBLICATIONS

Donald C. Hofer et al., "193 nm Photoresist R&D: The Risk & Challenge", Journal of Photopolymer Science and Technology, Vo.9, No. 3 (1996), pp. 387-397.

Hiroshi Ito et al., "Applications of Photoinitiators to the Design of Resists for Semiconductor Manufacturing", American Chemical Society 1984, vol. 242, pp. 11-23.

Satoshi Takechi et al., "Alicyclic Polymer for ArF and KrF excimer Resist Based on Chemical Amplification", Journal of Photopolymer Science and Technology, vol. 5, No. 3 (1992, pp. 439-446.

R.D. Allen et al., "Resolution and Etch Resistance of a Family of 193 nm Positive Resists", Journal of Photopolymer Science and Technology, vol. 8, No. 4, 1995, pp. 623-636.

R.M. Houlihan et al., "Synthesis of Cycloolefin-Maleic Anhydride Alternating Copolymers for 193 nm Imaging", American Chemical Society, Macromolecules vol. 30, 1997, pp. 6517-6524.

R.D. Allen et al., "Progress in 193 nm Positive Resists", Journal of Photopolymer Science and Technology, vol. 9, No. 3, 1996, pp. 465-575.

* cited by examiner

UNSATURATED MONOMERS, POLYMERS, CHEMICALLY-AMPLIFIED RESIST COMPOSITION, AND PROCESS OF PATTERN FORMATION

FIELD OF THE INVENTION

The invention relates to a polymer including a novel bridged alicyclic γ-lactone structure, and more particularly to a polymer suitable for a chemically-amplified resist composition to be exposed to far ultra-violet rays having a wavelength of 220 nanometers or smaller. The invention relates further to an unsaturated monomer useful as raw material monomer of which the polymer is composed, a chemically-amplified resist composition containing the polymer, and a method of forming a pattern.

DESCRIPTION OF THE RELATED ART

In a field of manufacturing various electronic devices such as a semiconductor device in which half-micron order patterns are required to form, an electric device is now required to have higher densification and integration. Thus, an improved lithography technique for forming a minuter pattern on a substrate is required for satisfying such a requirement.

In particular, photolithography employing an ArF excimer laser (193 nm) has been suggested for manufacturing a DRAM having an integration of 1 Gbit or higher which is necessary to form a pattern of 0.13 micrometers or smaller, for instance, in Donald C. Hofer et al., "193 nm Photoresist R&D: The Risk & Challenge", Journal of Photopolymer Science and Technology Vol. 9, No. 3 (1996), pp. 387–397.

Hence, there is now expected to develop a new resist to be employed for photolithography in which ArF excimer laser is to be used.

Such a resist to be exposed to ArF laser beams is required to enhance cost performance of laser beams, because a gas from which laser beams are radiated has short lifetime, and further because an equipment for radiating laser-beams is expensive. Thus, the resist is expected to have high sensitivity as well as a high resolution in response to a design rule getting smaller and smaller.

For instance, Japanese Patent Application Publication No. 59-45439 has suggested, as a chemically-amplified resist, a resist composition containing poly(p-tert-butoxycarbonyloxy-α-methylstyrene) and triphenylsulfonium.hexafluoroacenato. Such a chemically-amplified resist is employed broadly for a KrF excimer laser, for instance, as suggested in American Chemical Society Symposium Series, 1984, Vol. 242, pages 11–23, reported by Hiroshi Ito and C. Grant Willson.

A chemically-amplified resist is characterized by that proton acid is generated when a photo acid generator contained therein is exposed to light, and the thus generated proton acid causes acid catalyst reaction with a resist resin when the proton acid is headed after the exposure thereof to light. Thus, a chemically-amplified resist can have quite higher sensitivity in comparison with a prior resist which has an optical reaction efficiency, defined as reaction per a photon, of smaller than one (1). Presently, most of newly developed resists are chemically amplified resists.

In lithography in which light beams having a wavelength equal to or smaller than 220 nanometers, such as ArF excimer laser beams, are used, a resist is required to have high transparency to light having a wavelength equal to or smaller than 220 nanometers, and resistance to dry etching.

Photoresists used for g-line having a wavelength of 438 nm, i-line having a wavelength of 365 nm or KrF excimer laser having a wavelength of 248 nm are composed of resins including aromatic rings in a unit structure, such as novolak resin or poly (p-vinylphenol). A dry etching resistance of such aromatic rings gives an etching resistance to the resins.

However, a resin including aromatic rings quite intensively absorbs light having a wavelength equal to or shorter than 220 nanometers. Hence, if a photoresist composed of a resin including aromatic rings therein is used in a photolithography in which light beams having a wavelength equal to or shorter than 220 nanometers such as KrF excimer laser beams (193 nm) are used, most of the light beams is absorbed at a surface of the resist, and accordingly, cannot reach a substrate with the result that a minute resist pattern cannot be formed.

Accordingly, it is quite difficult to apply a resin including presently used aromatic rings to a photolithography in which light having a wavelength equal to or shorter than 220 nanometers is used. Thus, there is a need for a resist which does not include aromatic rings therein, which is transparent to light having a wavelength equal to or smaller than 220 nanometers, and which has resistance to etching.

As a polymer having transparency to ArF excimer laser beams having a wavelength of 193 nanometers and further having resistance to dry-etching, there have been suggested a copolymer having adamantylmethacrylate units which are alicyclic polymer, in Takechi et al., Journal of Photopolymer Science and Technology, 1992, Vol. 5, No. 3, pp. 439–446, a copolymer having isobornylmethacrylate units, in R. D. Allen et al., Journal of Photopolymer Science and Technology, 1995, Vol. 8, No. 4, pp. 623–636, a resin including norbornene-maleic anhydride alternating copolymers, in F. M. Houlihan et al., Macromolecules 1997, Vol. 30, pp. 6517–6524, and tertiary-butyl ester protecting group in R. D. Allen et al., Journal of Photopolymer Science and Technology, 1996, Vol. 9, No. 4, pp. 465–474.

However, monomers including alicyclic groups herein such as those mentioned above do not have polar groups (for instance, carboxyl groups or hydroxy groups) having adhesion to a substrate. Hence, monopolymer of monomers having alicyclic groups has intensive hydrophobic nature, and poor adhesion to a substrate (for instance, a silicon substrate), resulting in that a uniformly coated film cannot be well reproduced.

In addition, residues containing adamantine, isobonyl or menthyl therein, having resistance to dry etching, do not have residues which can exhibit a difference in solubility between before and after exposure to light. Hence, if monopolymer of these monomers are used, it would be difficult to form a pattern by exposing them to light.

This problem can be solved by copolymerizing those monomers with comonomers which can exhibit the solubility difference, such as t-butylmethacrylate or tetrahydromethacrylate, or with comonomers which have adhesion to a substrate, such as methacrylic acid.

Though the resultant copolymer has to contain comonomers therein at about 50 mol %, the copolymer could have insufficient resistance to dry etching, because of low resistance of a comonomer unit to dry etching.

The resist including norbornene—maleic anhydride alternating copolymers could have poor adhesion to a substrate, because of no polar groups in norbornene rings. In order to enhance adhesion to a substrate, it would be necessary, for instance, to copolymerize the resist with comonomers having adhesion to a substrate, such as acrylic acid.

However, the resultant copolymer might have insufficient resistance to dry etching.

Polymers including a lactone structure have been suggested as a photoresist material for use of ArF excimer laser beams (193 nm), which provides excellent resistance to etching and adhesion to a substrate, in Japanese Patent Application Publications Nos. 2000-159758, 2001-242627, and 2002-53571. Furthermore, Japanese Patent Application Publication No. 2001-296661 has suggested a polymer including a lactone structure as a material of which a photoresist is composed for use of ArF excimer laser beams (193 nm) and which has improved light-exposure margins.

However, there are not found any reports indicating that 4-oxo-5-oxatetracyclo [$7.2.1.0^{2,8}.0^{3,7}$] dodecyl skeleton (n=1 and X represents —CH$_2$—), 3-oxo-4-oxatricyclo [$5.2.1.0^{2,6}$] nonyl skeleton (n=0 and X represents —CH$_2$—) both defined in accordance with the later-mentioned general formula (III), 4-oxo-5-oxatetracyclo [$7.2.1.0^{2,8}.0^{3,7}$] dodecane-10,11-diyl skeleton defined in accordance with the later-mentioned general formula (IV), and 3-oxo-4-oxatricyclo [$5.3.0.0^{2,6}$] decane-8,10-dimethylene skeleton defined in accordance with the later-mentioned general formula (V), as well as the above-mentioned conventional materials, are useful for a chemically-amplified resist.

Though many suggestions have been made with respect to a chemically-amplified resist, as mentioned above, further improvement is required.

SUMMARY OF THE INVENTION

In view of the above-mentioned problems, it is an object of the present invention to provide a chemically-amplified resist composition having high transparency to light having a wavelength of 220 nanometers or smaller, resistance to etching, and adhesion to a substrate.

It is further an object of the present invention to provide a polymer (a resin of which a resist is composed) to be used for the chemically-amplified resist composition, unsaturated monomer thereof, and a method of forming a pattern through the use of the chemically-amplified resist composition.

In order to accomplish the above-mentioned objects, there is provided a (metha)acrylate derivative having a bridged alicyclic γ-lactone structure defined in the general formula (I):

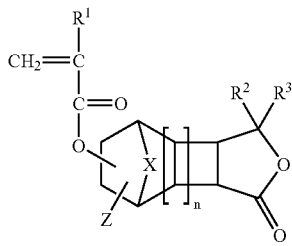

(I)

In the general formula (I), $R^1$ represents one of a hydrogen atom and a methyl group, $R^2$ and $R^3$ each represents one of a hydrogen atom and an alkyl group having a carbon number in the range of 1 to 6 both inclusive, or $R^2$ and $R^3$ link each other, and each represents an alkylene group having a carbon number in the range of 1 to 6 both inclusive and cooperating with a carbon atom to which $R^2$ and $R^3$ link to define a ring, X represents one of —CH$_2$— and —O—, Z represents one of a hydrogen atom and a methyl group, and n represents one of 0 and 1 wherein when n represents 0 and X represents —CH$_2$—, $R^2$ and $R^3$ each represents a carbon number in the range of 1 to 6 both inclusive.

There is further provided an unsaturated monomer having a bridged alicyclic γ-lactone structure defined in the general formula (II):

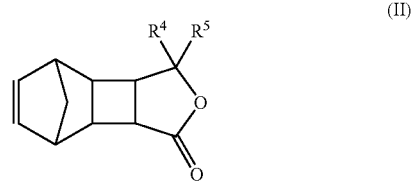

(II)

In the general formula (II), $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

There is still further provided a polymer resulted from polymerizing or copolymerizing a monomer composition containing at least one of the above-mentioned (metha) acrylate derivative and the above-mentioned unsaturated monomer.

There is yet further provided a polymer including at least one of a repeated structural unit having a bridged alicyclic γ-lactone structure defined in the general formula (III), a repeated structural unit having a bridged alicyclic γ-lactone structure defined in the general formula (IV), and a repeated structural unit having a bridged alicyclic γ-lactone structure defined in the general formula (V).

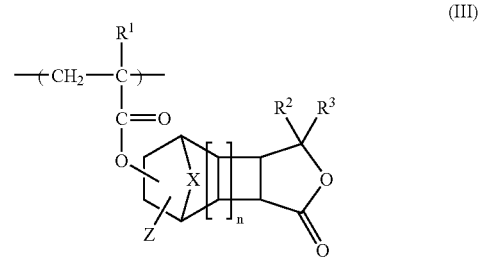

(III)

In the general formula (III), $R^1$ represents one of a hydrogen atom and a methyl group, $R^2$ and $R^3$ each represents one of a hydrogen atom and an alkyl group having a carbon number in the range of 1 to 6 both inclusive, or $R^2$ and $R^3$ link each other, and each represents an alkylene group having a carbon number in the range of 1 to 6 both inclusive and cooperating with a carbon atom to which $R^2$ and $R^3$ link to define a ring, X represents one of —CH$_2$— and —O—, Z represents one of a hydrogen atom and a methyl group, and n represents one of 0 and 1 wherein when n represents 0 and X represents —CH$_2$—, $R^2$ and $R^3$ each represents a carbon number in the range of 1 to 6 both inclusive.

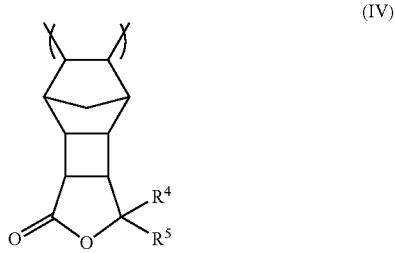

(IV)

In the general formula (IV), $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

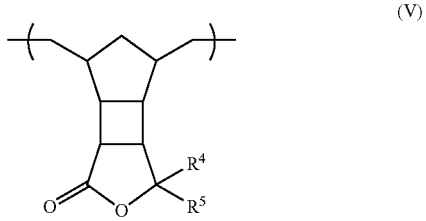

(V)

In the general formula (V), $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

In the above-mentioned polymer, the repeated structural unit defined in accordance with the general formula (III), the repeated structural unit defined in accordance with the general formula (IV), and the repeated structural unit defined in accordance with the general formula (V) are not always necessary to be identical with one another. The polymer may contain two or more repeated structural units selected from them. In the polymer, each of the structural units may have any sequence. Accordingly, the polymer may be a random copolymer, an alternating copolymer or a block copolymer.

It is preferable that a content ratio of the repeated structural unit defined in the general formula (III), (IV) or (V) to the polymer in its entirety is in the range of 5 to 100 mol % both inclusive.

It is preferable that a weight-average molecular weight of the polymer is in the range of 2,000 to 200,000 both inclusive.

The present invention further provides a chemically-amplified resist composition containing one of the above-mentioned polymers.

It is preferable that the chemically-amplified resist composition contains one of the above-mentioned polymers, and a photo acid generator which generates acid when exposed to light.

It is preferable in the chemically-amplified resist composition that a content of the photo acid generator is in the range of 0.2 to 30 mass % both inclusive relative to a total content of the polymer and the photo acid generator.

It is preferable that the photo acid generator generates acid when light having a wavelength in the range of 180 to 220 nanometers both inclusive is irradiated thereto.

The present invention further provides a method of forming a pattern, including at least the steps, in sequence, of coating the above-mentioned chemically-amplified resist composition onto a substrate, baking the chemically-amplified resist composition, exposing the chemically-amplified resist composition to light having a wavelength in the range of 180 to 220 nanometers both inclusive, baking the chemically-amplified resist composition, and developing the chemically-amplified resist composition.

As light to which the chemically-amplified resist composition is exposed, there may select ArF excimer laser beams, for instance.

Herein, the term "(co)polymerization" means monopolymerization or copolymerization, as usually used.

The polymer in accordance with the present invention includes, among bridged alicyclic lactone skeletons, 4-oxo-5-oxatetracyclo [$7.2.1.0^{2,8}.0^{3,7}$] dodecyl skeleton (n=1), 3-oxo-4-oxatricyclo [$5.2.1.0^{2,6}$] nonyl skeleton (n=0) both defined in accordance with the general formula (III), 4-oxo-5-oxatetracyclo [$7.2.1.0^{2,8}.0^{3,7}$] dodecane-10,11-diyl skeleton defined in accordance with the general formula (IV), and 3-oxo-4-oxatricyclo [$5.3.0.0^{2,6}$] decane-8,10-dimethylene skeleton defined in accordance with the general formula (V).

Hence, the chemically-amplified resist composition including the polymer in accordance with the present invention has high transparency to light having a wavelength of 220 nanometers or smaller, high resistance to etching and excellent adhesion to a substrate. The reasons therefore are considered as follows.

First, the repeated structural structures defined in accordance with the above-mentioned general formula (III), (IV) and (V) do not include aromatic rings. Hence, the chemically-amplified resist composition can have high transparency to light having a wavelength of 220 nanometers or smaller. In general, a polymer not including aromatic rings can have high transparency to light having a wavelength of 220 nanometers or smaller.

Second, the repeated structural structures defined in accordance with the above-mentioned general formula (III), (IV) and (V) include a bridged alicyclic structure having a high carbon-density, that is, tetracyclo [$7.2.1.0^{2,8}.0^{3,7}$] dodecane skeleton, tricyclo [$5.2.1.0^{2,6}$] nonane skeleton or tricyclo [$5.3.0.0^{2,6}$] decane skeleton. Hence, the chemically-amplified resist composition can have resistance to dry etching.

Third, the repeated structural structures defined in accordance with the above-mentioned general formula (III), (IV) and (V) include a γ-lactone structure. Hence, the chemically-amplified resist composition can have higher polarity than conventional ones, and accordingly, have more excellent adhesion to a substrate.

A lactone structure generally has a higher dielectric constant than the same of an ester structure, an ether structure and an alcohol structure.

For instance, according to Chemistry Handbook edited by Japan Chemistry Academy, Basic II, 3rd edition, 1984, pp. 502–504, comparison being made among compositions having a carbon number of 4, a γ-butyrolactone has a dielectric constant of 39, an ethyl acetate has a dielectric constant of 6.02, a diethyl ether has a dielectric constant of 4.335, and a 1-butanol has a dielectric constant of 17.51. Among lactone structures, a γ-lactone structure has an optimal dielectric constant, and hence, it can accomplish particularly excellent adhesion to a substrate.

As mentioned above, the repeated structural structures defined in accordance with the above-mentioned general formula (III), (IV) and (V) include both a bridged alicyclic structure and a γ-lactone structure, they can accomplish desired transparency to light having a wavelength of 220 nanometers or smaller, resistance to etching, and adhesion to a substrate, by virtue of the multiplier effect of a molecular structure and a dielectric constant.

The advantages obtained by the aforementioned present invention will be described hereinbelow.

The resin having a repeated structural unit including a bridged alicyclic γ-lactone structure in accordance with the present invention presents chemically-amplified resist composition which is excellent in resistance to etching, transparency to light having a wavelength of 220 nm or smaller, resolution, and adhesion to a substrate. Furthermore, the chemically-amplified resist composition makes it possible to form a minute pattern necessary for fabrication of a semiconductor device.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS (1) Unsaturated Monomer of which the Polymer in Accordance with the Present Invention is Composed The polymer in accordance with the present invention is obtained by (co)polymerizing both or one of a (metha) acrylate derivative having a bridged alicyclic γ-lactone structure defined in accordance with the general formula (I) and a monomer composition including an unsaturated monomer having a bridged alicyclic γ-lactone structure defined in accordance with the general formula (II).

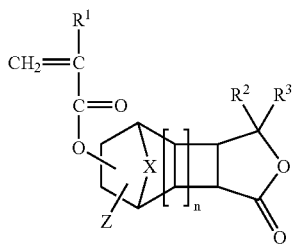

(I)

In the general formula (I), $R^1$ represents one of a hydrogen atom and a methyl group, $R^2$ and $R^3$ each represents one of a hydrogen atom and an alkyl group having a carbon number in the range of 1 to 6 both inclusive, or $R^2$ and $R^3$ link each other, and each represents an alkylene group having a carbon number in the range of 1 to 6 both inclusive and cooperating with a carbon atom to which $R^2$ and $R^3$ link to define a ring, X represents one of —$CH_2$— and —O—, Z represents one of a hydrogen atom and a methyl group, and n represents one of 0 and 1 wherein when n represents 0 and X represents —$CH_2$—, $R^2$ and $R^3$ each represents a carbon number in the range of 1 to 6 both inclusive.

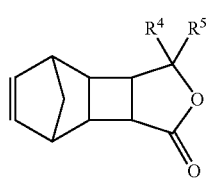

(II)

In the general formula, $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

The alkyl group having a carbon number in the range of 1 to 6 both inclusive may be straight-chain type one or branch-type one. It is preferable that the alkyl group has a carbon number of 1 or 2.

Specifically, as an alkyl group having a carbon number in the range of 1 to 6 both inclusive, there may be selected from a methyl group, an ethyl group, a n-propyl group, an isopropyl group, a n-butyl group, an isobutyl group, a n-pentyl group, or a n-hexyl group.

The alkylene group having a carbon number in the range of 1 to 6 both inclusive may be branch-type one, but preferably straight-chain type one. The alkylene group mentioned herein includes a polymethylene group. It is preferable that the alkylene group has a carbon number of 4 or 5.

As an alkylene group having a carbon number in the range of 1 to 6 both inclusive, there may be selected from a propylene group (a trimethylene group) [—$(CH_2)_3$—], a butylene group (a tetramethylene group) [—$(CH_2)_4$—], or a penthylene group (a pentamethylene group) [—$(CH_2)_5$—].

As the unsaturated monomer defined in accordance with the general formula (I), there may be selected from the followings.

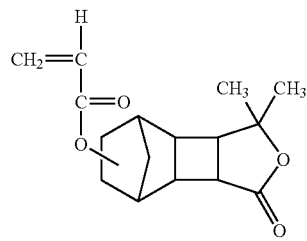

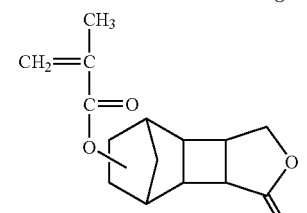

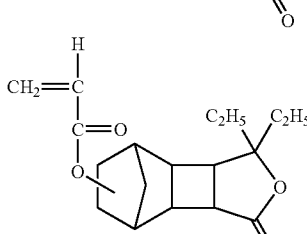

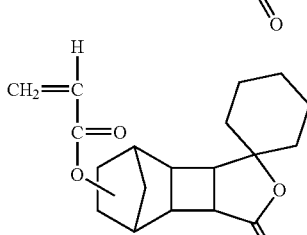

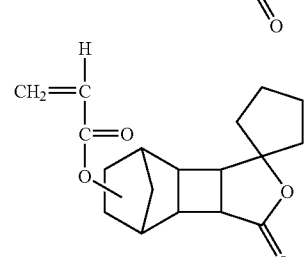

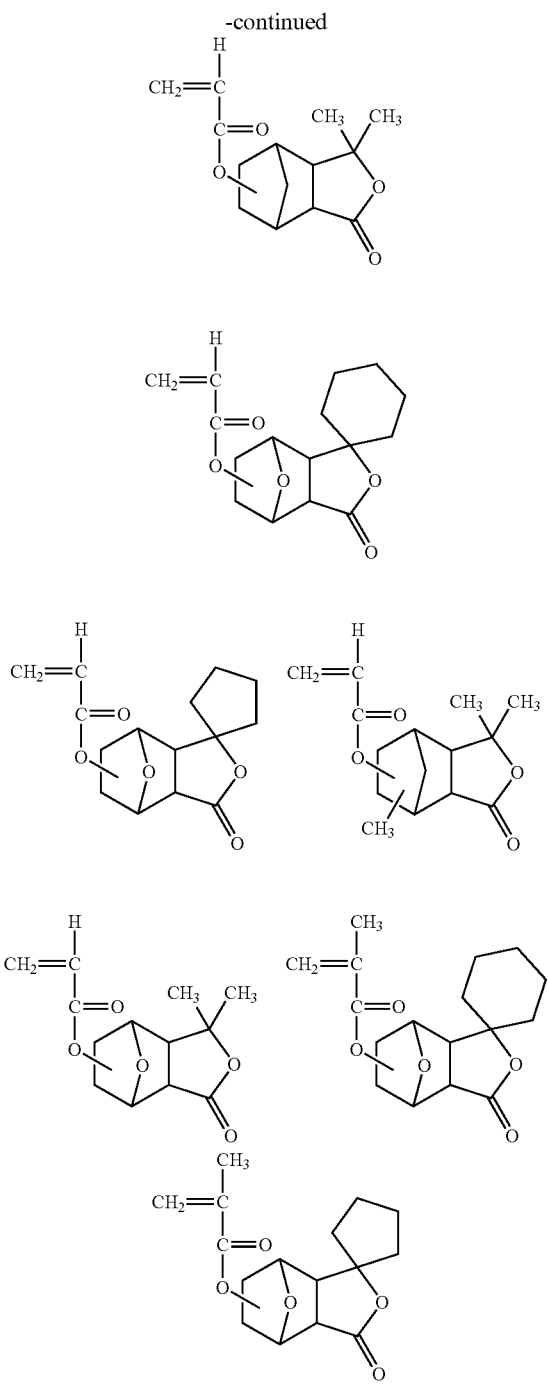

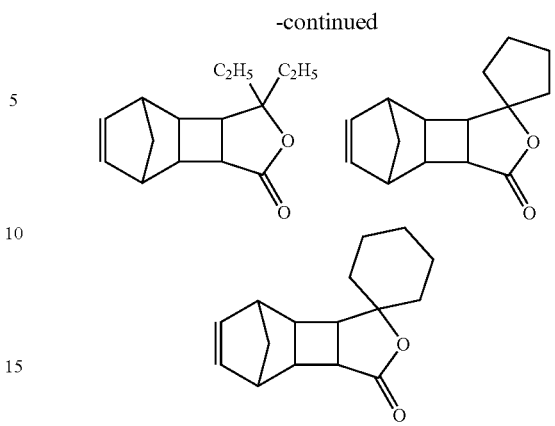

In the general formula (I), when n is equal to one (1), it is particularly preferable that each of $R^2$ and $R^3$ represents a hydrogen atom, a methyl group, an ethyl group or an alkylene group having a carbon number of 4 or 5, and when n is equal to zero (0), it is particularly preferable that each of $R^2$ and $R^3$ represents a methyl group, an ethyl group or an alkylene group having a carbon number of 4 or 5.

In the general formula (II), it is particularly preferable that each of $R^4$ and $R^5$ represents a methyl group, an ethyl group or an alkylene group having a carbon number of 4 or 5.

(2) Method of Manufacturing the Monomer in Accordance with the Present Invention The monomer defined in accordance with the above-mentioned general formula (II) can be manufactured, for instance, by causing tricycle [4.2.1.02,5]-7-nonene-3,4-dicarboxylic acid anhydride to react with Grignard reagent, and treating the resultant with acid.

The monomer defined in accordance with the above-mentioned general formula (I) can be manufactured, for instance, by causing either the composition defined in accordance with the general formula (II) or tricycle 5-norbornene-2,3-dicarboxylic acid anhydride to react with Grignard reagent, treating the resultant with acid to generate lactone compound, and either causing the lactone compound to react with (metha)acrylic acid under existence of acid catalyst, or turning the lactone compound into hydroxy compound in hydroborasion reaction, and causing the resultant to react with (metha)acryloilchloride under existence of basic catalyst.

(3) Polymer in Accordance with the Present Invention

The polymer in accordance with the present invention is obtained by (co)polymerizing both or one of an unsaturated monomer having a bridged alicyclic γ-lactone structure defined in accordance with the general formula (I) and a monomer composition including an unsaturated monomer having a bridged alicyclic γ-lactone structure defined in accordance with the general formula (II), and includes at least one of a repeated structural unit having the bridge alicyclic γ-lactone structure defined in accordance with the general formula (III), a repeated structural unit having the bridge alicyclic γ-lactone structure defined in accordance with the general formula (IV), and a repeated structural unit having the bridge alicyclic γ-lactone structure defined in accordance with the general formula (V).

As the unsaturated monomer defined in accordance with the general formula (II), there may be selected from the following monomers.

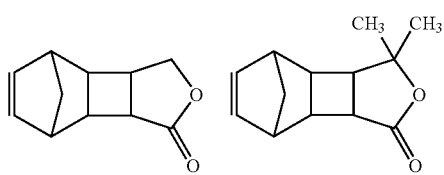

The repeated structural unit defined in accordance with the general formula (III) is derived from the monomer defined in accordance with the general formula (I). Each of the repeated structural units defined in accordance with the general formulas (IV) and (V) is derived from the monomer defined in accordance with the general formula (II).

The polymer in accordance with the present invention, having such a structure as mentioned above is suitable for a resin of which a resist is composed.

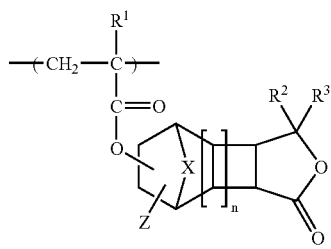
(III)

In the general formula (III), $R^1$ represents one of a hydrogen atom and a methyl group, $R^2$ and $R^3$ each represents one of a hydrogen atom and an alkyl group having a carbon number in the range of 1 to 6 both inclusive, or $R^2$ and $R^3$ link each other, and each represents an alkylene group having a carbon number in the range of 1 to 6 both inclusive and cooperating with a carbon atom to which $R^2$ and $R^3$ link to define a ring, X represents one of —CH$_2$— and —O—, Z represents one of a hydrogen atom and a methyl group, and n represents one of 0 and 1 wherein when n represents 0 and X represents —CH$_2$—, $R^2$ and $R^3$ each represents a carbon number in the range of 1 to 6 both inclusive,

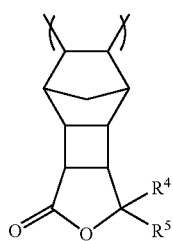
(IV)

In the general formula (IV), $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

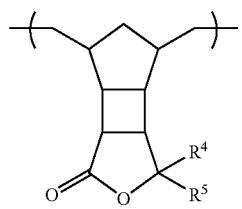
(V)

In the general formula (V), $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

The alkyl group having a carbon number in the range of 1 to 6 both inclusive may be straight-chain type one or branch-type one. It is preferable that the alkyl group has a carbon number of 1 or 2.

Specifically, as an alkyl group having a carbon number in the range of 1 to 6 both inclusive, there may be selected from a methyl group, an ethyl group, a n-propyl group, an isopropyl group, a n-butyl group, an isobutyl group, a n-pentyl group, or a n-hexyl group.

The alkylene group having a carbon number in the range of 1 to 6 both inclusive may be branch-type one, but preferably straight-chain type one. The alkylene group mentioned herein includes a polymethylene group. It is preferable that the alkylene group has a carbon number of 4 or 5.

As an alkylene group having a carbon number in the range of 1 to 6 both inclusive, there may be selected from a propylene group (a trimethylene group) [—(CH$_2$)$_3$—], a butylene group (a tetramethylene group) [—(CH$_2$)$_4$—], or a penthylene group (a pentamethylene group) [—(CH$_2$)$_5$—].

As the repeated structural unit defined in accordance with the general formula (III), there may be selected from the followings.

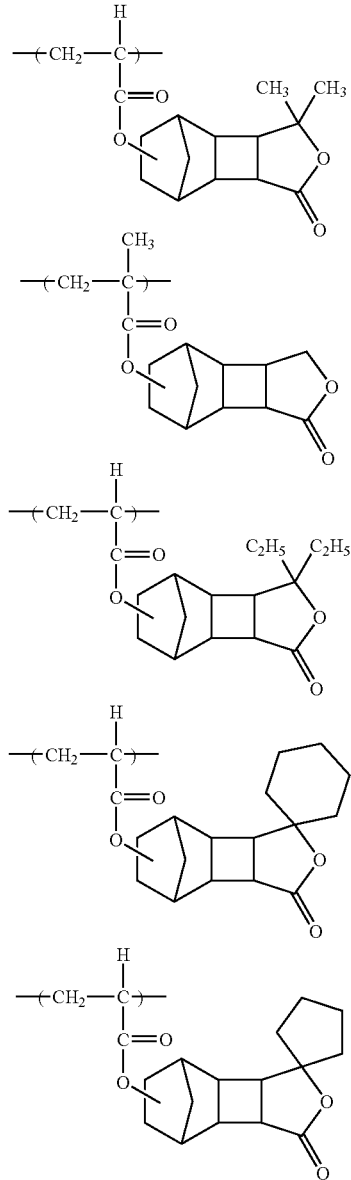

-continued
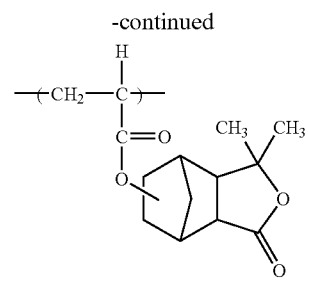
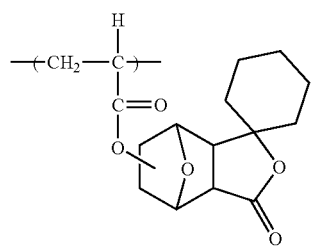
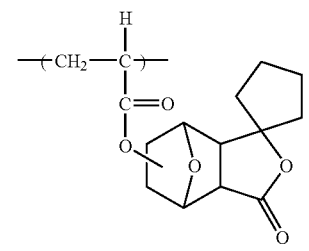
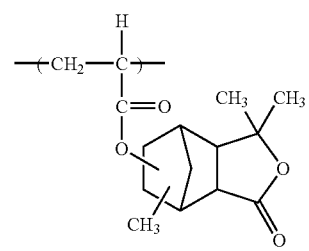
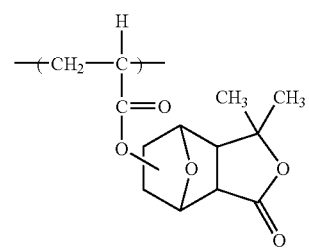
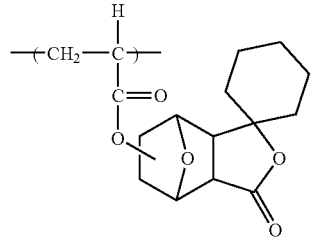
-continued
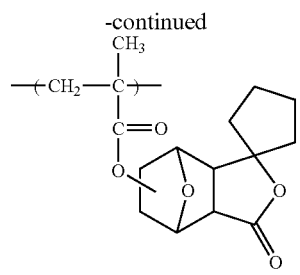
As the repeated structural unit defined in accordance with the general formula (IV), there may be selected from the followings.
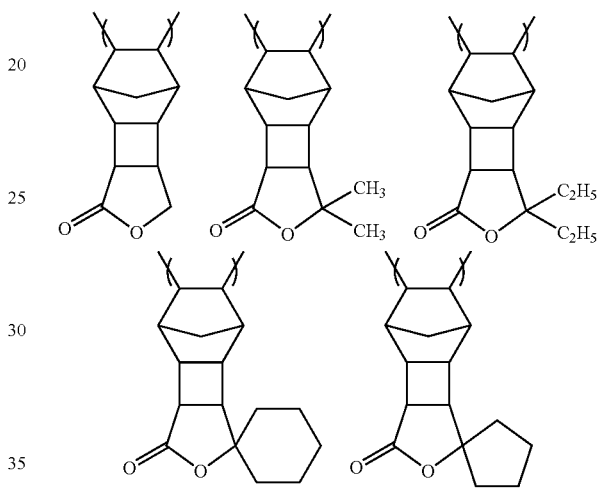
As the repeated structural unit defined in accordance with the general formula (V), there may be selected from the followings.
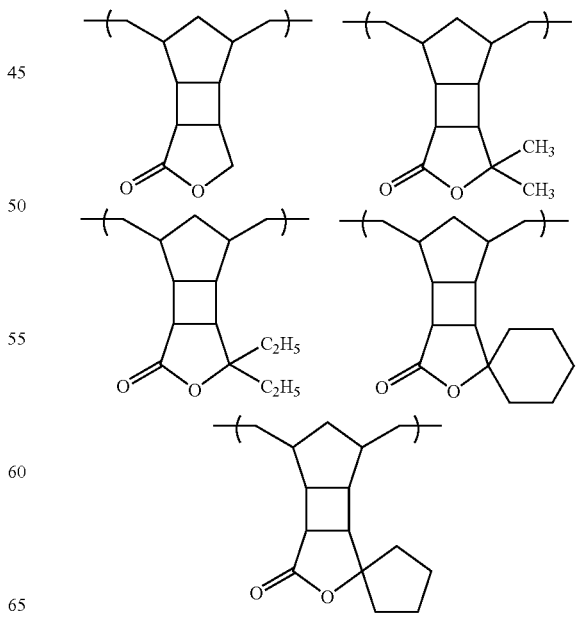

In the general formula (III), when n is equal to one (1), it is particularly preferable that each of $R^2$ and $R^3$ represents a hydrogen atom, a methyl group, an ethyl group or an alkylene group having a carbon number of 4 or 5, and when n is equal to zero (0), it is particularly preferable that each of $R^2$ and $R^3$ represents a methyl group, an ethyl group or an alkylene group having a carbon number of 4 or 5.

In the general formulas (IV) and (V), it is particularly preferable that each of $R^4$ and $R^5$ represents a methyl group, an ethyl group or an alkylene group having a carbon number of 4 or 5.

One or more unsaturated monomers defined in accordance with the general formula (I) may be polymerized with one or more unsaturated monomers defined in accordance with the general formula (II).

The unsaturated monomers defined in accordance with the general formula (I) are not always necessary to be identical with one another. Two or more monomers may be used, if they are defined in accordance with the general formula (I).

The unsaturated monomers defined in accordance with the general formula (II) are not always necessary to be identical with one another. Two or more monomers may be used, if they are defined in accordance with the general formula (II).

In the polymer in accordance with the present invention, the repeated structural unit defined in accordance with the general formula (III), the repeated structural unit defined in accordance with the general formula (IV), and the repeated structural unit defined in accordance with the general formula (V) are not always necessary to be identical with one another. The polymer may contain two or more repeated structural units, if they are defined in accordance with the above-mentioned general formulas.

In the polymer in accordance with the present invention, each of the repeated structural units may have any sequence. Accordingly, the polymer may be a random copolymer, an alternating copolymer or a block copolymer.

If necessary, it would be possible to accomplish broader characteristics by copolymerizing two or more monomers, and using a polymer including two or more repeated structural units.

The monopolymer of the unsaturated monomer defined in accordance with the general formula (I) or the monopolymer of the unsaturated monomers defined in accordance with the general formula (II), or the copolymer of at least one of two or more unsaturated monomers defined in accordance with the general formula (I) and two or more unsaturated monomers defined in accordance with the general formula (II) has high transparency to light having a wavelength of 220 nanometers or smaller, resistance to etching, and adhesion to a substrate.

By copolymerizing the polymer with other comonomers, the polymer in accordance with the present invention can have a structural unit including groups which can decompose acid derived from a photo acid generator, and a structural unit for accomplishing broader characteristics in a resin of which a chemically-amplified resist is composed, as well as the repeated structural units defined in accordance with the general formulas (III), (IV) and (V).

In the above-mentioned case, each of the structural units may have any sequence. Accordingly, the polymer may be a random copolymer, an alternating copolymer or a block copolymer.

As a repeated structural unit derived from a comonomer to be copolymerized together, any one or more of the structural units defined in accordance with the general formulas (VI-a) to (VI-d) may be preferably selected in view that broad characteristics can be accomplished and associated monomers have sufficient polymerizability.

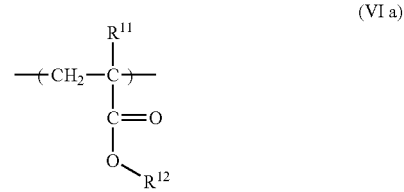

(VI a)

In the general formula (VI-a), $R^{11}$ represents a hydrogen atom or a methyl group, and $R^{12}$ represents a hydrogen atom, a group decomposable by acid, a bridged alicyclic hydrocarbon radical including a group decomposable by acid and having a carbon number in the range of 7 to 13 both inclusive, a hydrocarbon radical having a carbon number in the range of 7 to 12 both inclusive, a bridged alicyclic hydrocarbon radical including a hydroxy group or a carboxy group, and having a carbon number in the range of 7 to 13 both inclusive, or a 2,6-norbornanecarbolactone-5-yl group.

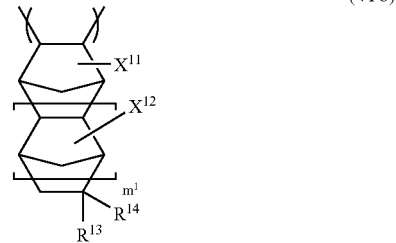

(VI b)

In the general formula (VI-b), $R^{13}$ represents a hydrogen atom or a methyl group, and $R^{14}$ represents a hydrogen atom, a hydroxy group, a hydroxyalkyl group, a carboxy group, or an acid-decomposable organic group decomposable by acid to generate a carboxy group, and having a carbon number of 20 or smaller. Each of $X^{11}$ and $X^{12}$ represents a hydrogen atom or a methyl group, and m1 represents 0 or 1.

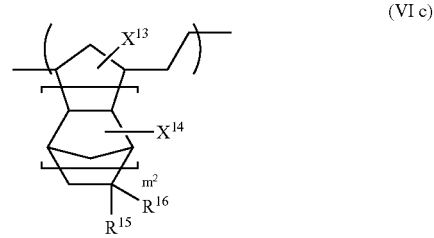

(VI c)

In the general formula (VI-c), $R^{15}$ represents a hydrogen atom or a methyl group, and $R^{16}$ represents a hydrogen atom, a hydroxy group, a hydroxyalkyl group, a carboxy group, or an acid-decomposable organic group decomposable by acid to generate a carboxy group, and having a carbon number of 20 or smaller. Each of $X^{13}$ and $X^{14}$ represents a hydrogen atom or a methyl group, and $m^2$ represents 0 or 1.

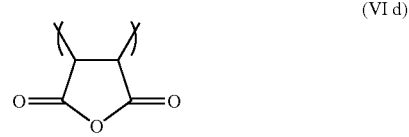

(VI d)

As a group decomposable by acid, there may be selected from a t-butyl group, a tetrahydropyran-2-yl group, a tetrahydrofuran-2-yl group, a 4-metoxytetrahydropyran-4-yl group, a 1-ethoxyethyl group, a 1-butoxyethyl group, a 1-propoxyethyl group, a 3-oxocyclohexyl group, a 2-methyl-2-adamanthyl group, a 2-ethyl-2-adamanthyl group, a 1-methyl-1-adamanthyl group, a 8-methyl-8-tricyclo [5.2.1.0$^{2,6}$] decyl group, a 1,2,7,7-tetramethyl-2-norbornyl group, a 2-acetoxymenthyl group, a 2-hydroxymenthyl group, and a 1-methyl-1-cyclohexylethyl group.

As a bridged alicyclic hydrocarbon radical including a group decomposable by acid and having a carbon number in the range of 7 to 13 both inclusive, there may be selected from a t-butoxycarbonyloxytetracyclododecyl group or a t-butoxycarbonyloxynorbornyl group, as suggested in Japanese Patent No. 2856116.

As a hydrocarbon radical having a carbon number in the range of 1 to 12 both inclusive, there may be selected from a methyl group, an ethyl group, a n-propyl group, an isoproplyl group, a n-butyl group, an isobutyl group, a t-butyl group, a cyclohexyl group, a tricycle [5.2.1.0$^{2,6}$] decyl group, an adamanthyl group, a norbonyl group, an isobonyl group, and a tetracyclo [4.4.0.1$^{2,5}$·1$^{7,10}$] dodecyl group.

As a bridged alicyclic hydrocarbon radical including a hydroxy group or a carboxy group, and having a carbon number in the range of 7 to 13 both inclusive, there may be selected from a hydroxyadamanthyl group, a dihydroxyadamanthyl group, a hydroxynorbornyl group, a hydroxytetracyclododecyl group, a carboxyadamanthyl group, a carboxynorbornyl group, and a carboxytetracyclododecyl group.

As a hydroxyalkyl group, a hydroxymethyl group or a hydroxyethyl group may be used.

As an acid-decomposable organic group decomposable by acid to generate a carboxy group, and having a carbon number of 20 or smaller, there may be selected from a t-butoxycarbonyl group, a tetrahydropyranyloxycarbonyl group, a 4-methoxytetrahydropyranyloxycarbonyl group, a 1-ethoxyethoxycarbonyl group, a tetrahydrofuranyloxycarbonyl group, a 1-butoxyethoxycarbonyl group, a 1-propoxyethoxycarbonyl group, a 3-oxocyclohexyloxycarbonyl group, a 2-methyl-2-adamanthyloxycarbonyl group, a 2-ethyl-2-adamanthyloxycarbonyl group, a 8-methyl-8-tricyclo [5.2.1.0$^{2,6}$] decyloxycarbonyl group, 1,2,7,7-tetramethyl-2-norbornyloxycarbonyl group, a 2-acetoxymenthyloxycarbonyl group, a 2-hydroxymenthyloxycarbonyl group, and a 1-methyl-1-cyclohexylethoxycarbonyl group.

It is preferable that a content ratio of the structural unit defined in the general formula (III), (IV) or (V) in the polymer in its entirety is in the range of 5 to 100 mol % both inclusive.

When the polymer is copolymerized with other comonomers, a content ratio of the structural unit defined in the general formula (III), (IV) or (V) in the resultant copolymer in its entirety is in the range of preferably 5 mol % or greater, more preferably 7 mol % or greater, and most preferably 10 mol % or greater.

A content ratio of the structural unit defined in the general formula (III), (IV) or (V) in the copolymer in its entirety is in the range of preferably 90 mol % or smaller, more preferably 80 mol % or smaller, and most preferably 70 mol % or smaller.

A weight-average molecular weight of the polymer in accordance with the present invention is in the range of 2,000 to 200,000 both inclusive regardless of whether the polymer is a monopolymer or a copolymer.

(4) Method of Manufacturing the Polymer in Accordance with the Present Invention The polymer having the above-mentioned structure, in accordance with the present invention, can be manufactures by a conventional polymerization process such as radical polymerization, anion polymerization, addition polymerization or ring opening metathesis polymerization.

In radical polymerization, the polymer can be manufactured by, for instance, adding suitable initiator (for instance, azobisisobutyronitrile (AIBN)) of radical polymerization to dry tetrahydrofuran in inert gas (for instance, argon or nitrogen) atmosphere, and heating and stirring the resultant at a temperature in the range of 50 to 70 degrees centigrade for 0.5 to 12 hours.

A volume of the initiator of radical polymerization may be determined to any volume. An organic solvent to be used is not to be limited to tetrahydrofuran, but any organic solvent may be used.

In addition polymerization, the polymer can be manufactured through the use of palladium compound such as ($\eta^3$-allyl) Pd (BF$_4$), ($\eta^3$-allyl) Pd (SbF$_6$), [Pd(CH$_3$CN)$_4$][BF$_4$]$_2$ as a catalyst in accordance with the method suggested by J. P. Mathew in Macromolecules, 1966, Vol. 29, pp. 2755–2763.

As an alternative, the polymer can be manufactured through the use of nickel compound such as bis(pentafluorophenyl) nickel toluene complex in accordance with the method suggested by T. Chiba et al. in Journal of Photopolymer Science and Technology, 2000, Vol. 13, No. 4, pp. 657–664.

In ring opening metathesis polymerization, the polymer can be manufactured by carrying out ring-opening polymerization through the use of a metathesis catalyst, and hydrogenating the resultant through the use of a noble-metal catalyst such as palladium.

As a metathesis catalyst, there may be selected from halides of transition metals such as tungsten (W), molybdenum (Mo), or rhenium (Re), specifically, from WCl$_6$, MoCl$_5$ and ReCl$_3$. A metathesis catalyst is not to be limited to those compounds. As a metathesis catalyst, there may be also used halides of the above-mentioned transition metals, and organic metal compounds such as organic aluminum compounds.

(5) The Chemically-Amplified Resist Compound in Accordance with the Present Invention The chemically-amplified resist compound in accordance with the present invention is composed of mixture of the above-mentioned polymer in accordance with the present invention and a photo acid generator which generates acid when exposed to light.

The chemically-amplified resist compound in accordance with the present invention generally further includes a solvent for solving the polymer and the photo acid generator. The polymer in accordance with the present invention may contain one or more solvents.

A photo acid generator to be used for the invention preferably generates an acid when exposed to light preferably having a wavelength equal to or smaller than 400 nm, and more preferably, in the range of 180 to 220 nm both inclusive.

In the present invention, any photo acid generator may be used if a mixture of the polymer and the photo acid generator is sufficiently soluble in a solvent, and further if it is possible to form a uniform coating film by means of a film-forming process such as a spin-coating process. One or more photo acid generators may be mixed in the invention.

Photo acid generators usable for reducing the present invention into practice may be selected, for instance, from any one of triphenylsulfonium salt derivatives, sulfonium salt derivatives suggested in Japanese Patent Application Publication No. 2001-294570, alkylsulfonium salt derivatives having a bridged cyclic alkyl group, suggested in Japanese Patent No. 2964990, dialkyl-2-oxoalkylsulfonium salt derivatives suggested in Japanese Patent Application Publication No. 2001-354669, trialkylsulfonium salt derivatives. diphenyliodonium salt derivatives, dialkylphenasyl-sulfonium salt derivatives, nitrobenzylsulfonate derivatives, sulfonate derivatives of N-hydroxysuccinimide.

A content of a photo acid generator is preferably 0.2 mass % or greater, and more preferably, 1 mass % or greater relative to a total mass of the polymer and the photo acid generator so as to accomplish sufficient sensitivity of the chemically-amplified resist composition and form a desired pattern.

Furthermore, the content of a photo acid generator is preferably 30 mass % or smaller, and more preferably 15 mass % or smaller so as to uniformly form a film and suppress generation of residue (scum) after development.

If necessary, a suitable solvent is used for preparing the chemically-amplified resist composition in accordance with the present invention.

In the present invention, any solvent may be used if it can well solve the polymer and the photo acid generator, and further if solution of the solvent can be uniformly coated onto an object by a film-coating process such as a spin-coating process. A single solvent or a mixture of two or more solvents may be used.

Specifically, a solvent to be used in the invention is selected from any one of n-propyl alcohol, isopropyl alcohol, n-butyl alcohol, tert-butyl alcohol, propyleneglycol-monomethylether acetate, propyleneglycolmonoethylether acetate, methyl lactate, ethyl lactate, 2-methoxybutyl acetate, 2-ethoxyethyl acetate, pyrubic acid methyl, pyrubic acid ethyl, 3-methoxypropionatemethyl, 3-methoxypropion-ateethyl, N-methyl-2-pyrrolidinone, cyclopentanone, cyclohexanol, methylethylketone, 1,4-dioxan, ethyleneglycol-monomethylether, ethylene glycolmonomethylether acetate, ethylene glycolmonoethylether, ethyleneglycolmonoisopropylether, diethyleneglycolmonomethylether, and diethyleneglycoldimethylether.

A content of a solvent in the chemically-amplified resist composition in accordance with the present invention, comprised of a polymer, a photo acid generator and a solvent, is determined in accordance with a thickness of a resist to be formed.

If necessary, the chemically-amplified resist composition in accordance with the present invention may include other components such as an agent for avoiding dissolution, basics, a surface active agent, pigments, a stabilizer, an agent for improving coating characteristic, and dyes.

(6) Method of Forming a Pattern, in Accordance with the Present Invention

Hereinbelow is explained an example of a method of forming a pattern in accordance with the present invention. The method may use the above-mentioned chemically-amplified resist composition in accordance with the present invention.

First, the chemically-amplified resist composition in accordance with the present invention is coated onto a substrate by a spin-coating process or any other suitable process.

Then, the substrate on which the chemically-amplified resist composition has been coated is baked (pre-baked) to thereby dry the coated film. Thus, there is formed a resist film on the substrate.

Then, the thus formed resist film is exposed through a photomask to light having a wavelength in the range of 180 to 220 nanometers both inclusive. As light to which the resist film is to be exposed is preferably ArF excimer laser beams.

After exposure to the light, the resist film is baked, and then, developed. Any conventional developing solution may be used. After development, if necessary, the substrate is rinsed with pure water. Thus, a resist pattern is formed on the substrate.

Then, the substrate on which the resist pattern has been formed is baked (post-baked).

EXAMPLES

Hereinbelow, the present invention is explained in detail in connection with examples. However, it should be noted that the present invention is not to be limited to those examples.

Unless otherwise indicated, reagents used are available ones having high purity.

Example 1

There was synthesized 4-oxo-5-oxatetracyclo [7.2.1.0$^{2,}$ 8.0$^{3,7}$]-10-dodecene having the structure indicated below, that is, a monomer defined in accordance with the general formula (II) wherein R$^4$ and R$^5$ each represents a hydrogen atom.

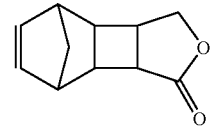

First, sodium boron hydride of 4.46 grams was dispersed in dry tetrahydrofuran (hereinafter, referred to simply as "THF") of 50 ml. Then, while cooled by ices, solution obtained by solving tricycle [4.2.1.0$^{2,5}$]-7-nonene-3,4-dicar-boxylic acid anhydride (synthesized in accordance with the method suggested in J. Am. Chem. Soc. Vol. 94, pp. 787–792) of 20 grams into THF of 100 ml was dropped to the mixture of sodium boron hydride and THF.

The resultant was stirred for two hours at room temperature, and then, 0.5N hydrochloric acid was added to the resultant to make the resultant acidic. Then, under a reduced pressure, a solvent was removed at 50 degrees centigrade. Then, diethyl ether of 200 ml was added to the residue, and then, washed with brine.

After the organic layer was dried with MgSO$_4$, diethyl ether was removed under a reduced pressure. Then, chloroform of 200 ml and further silica gel were added to the resultant to thereby remove impurities by absorption. Then, a solvent was removed under a reduced pressure. Then, the residue was recombined with ligroin. Thus, there was obtained a target material by 6 grams. The yield was 32%.

The measurement results of $^1$H-NMR (reference sample: CDCl$_3$) of the obtained target material were as follows.

δ:
0.1.4 (1H, d),
1.59 (1H, d),
1.94–1.98 (1H, m),
2.12–2.16 (1H, m),
2.44–2.51 (1H, m),
2.6 (1H, dd),
2.83 (1H, s),
2.94 (1H, s),
4.36 (1H, dd),
4.51 (1H, dd),
6.03 (1H, s).

Example 2

There was synthesized 4-oxo-5-oxa-6,6-dimethyltetracyclo [7.2.1.0$^{2,8}$.0$^{3,7}$]-10-dodecene having the structure indicated below, that is, a monomer defined in accordance with the general formula (II) wherein R$^4$ and R$^5$ each represents a methyl group.

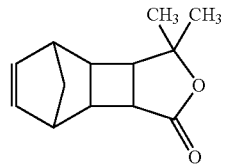

First, solution obtained by solving tricycle [4.2.1.0$^{2,5}$]-7-nonene-3,4-dicarboxylic acid anhydride of 20 grams into dry THF of 200 ml while cooled with ices was dropped to diethyl ether solution (3 mol/liter) of methylmagnesiumbromide of 110 ml in argon atmosphere.

The resultant was stirred for two hours at room temperature, and then, 10% hydrochloric acid was added to the resultant, while cooled with ices, to make the resultant acidic. Then, the resultant was stirred for an hour at 40 degrees centigrade. Then, diethyl ether of 200 ml was added to the resultant. Then, the organic layer was washed with 4% aqueous solution of sodium carbonate and further saturated brine in turn, and thereafter, was dried with magnesium sulfate.

Then, dimethyl ether was removed under a reduced pressure. Then, the residue was recombined with ligroin-toluene. Thus, there was obtained a target material by 6.92 grams. The yield was 32%.

The measurement results of $^1$H-NMR (reference sample: CDCl$_3$) of the obtained target material were as follows.
δ:
1.35 (3H, s),
1.37 (1H, d),
1.48 (3H, s),
1.57 (1H, d),
1.97–2.01 (1H, m),
2.06–2.1 (1H, m),
2.13–2.18 (1H, m),
2.71–2.75 (2H, m),
2.93 (1H, s),
6.03 (2H, s).

Example 3

There was synthesized acrylate having the structure indicated below, that is, acrylate defined in accordance with the general formula (I) wherein R$^1$ represents a hydrogen atom, R$^2$ and R$^3$ each represents a methyl group, X represents —CH$_2$—, Z represents a hydrogen atom, and n is equal to one (1).

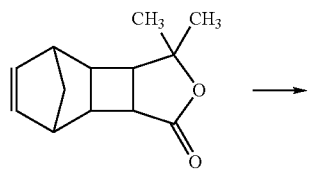

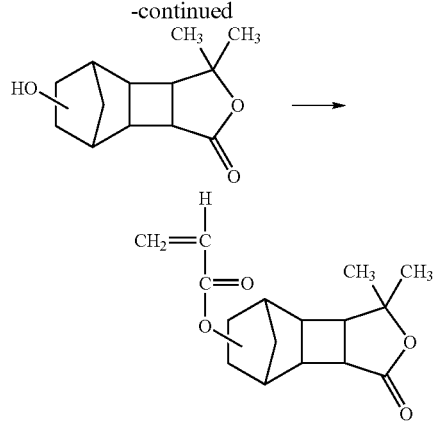

First, THF solution (1 mol/L) of BH$_3$ THF complex salt of 21 ml was dropped, while cooled with ices, into a solution obtained by solving the monomer of 7.8 grams obtained in Example 2 into dry THF of 200 ml.

The resultant was stirred for an hour while cooled with ices and further for an hour at room temperature, and then, water of 3 ml, NaOH aqueous solution (3 mol/L) of 7 ml, and 30% hydrogen peroxide solution of 4.6 ml were dropped in turn into the resultant.

Then, the resultant was stirred for two hours at room temperature. Then, diethyl ether of 100 ml was added to the resultant. Then, the diethyl ether organic layer was washed with saturated brine, and thereafter, was dried with magnesium sulfate. Then, a solvent was removed under a reduced pressure. Thus, there was quantitatively obtained alcohol.

Then, alcohol of 4.88 grams, N,N-dimethylaniline of 3.99 grams, and phenothiazine of 10 mg were solved into dry methylene chloride of 40 ml, and then, acryloil chloride of 2.38 grams were dropped into the resultant while cooled with ices. After the resultant was stirred for four hours at room temperature, diethylether of 150 ml was added to the resultant. Then, the resultant was washed with 0.5N hydrochloric acid, 3% aqueous solution of sodium carbonate and further brine, and thereafter, was dried with magnesium sulfate.

After a solvent was removed under a reduced pressure, the residue was purified in a silica-gel column (solvent for elution: hexane/ethyl acetate=2/1). Thus, there was obtained a target material, that is, acrylate by 2 grams in the form of transparent liquid. The yield was 33%.

The measurement results of $^1$H-NMR (reference sample: CDCl$_3$) of the obtained acrylate were as follows.
δ:
1.287, 1.292, 1.47, 1.49 (6H, s),
1.51–1.81 (4H, m),
2.1–2.49 (5H, m),
2.78–2.84 (1H, m),
4.52–4.59 (1H, m),
5.82 (1H, dd),
6.09 (1H, dd),
6.38 (1H, d).

The measurement results of 1R (KBr disc) were as follows.
1R (KBr disc):
2969 cm$^{-1}$ [ν(C—H)],
1766 cm$^{-1}$, 1722 cm$^{-1}$ [ν(C=O)],
1635 cm$^{-1}$, 1619 cm$^{-1}$ [ν(C=C)],
1274 cm$^{-1}$,
1194 cm$^{-1}$.

Example 4

There was synthesized acrylate having the structure indicated below, that is, acrylate defined in accordance with the general formula (I) wherein $R^1$ represents a hydrogen atom, $R^2$ and $R^3$ each represents a methyl group, X represents —$CH_2$—, Z represents a hydrogen atom, and n is equal to zero (0).

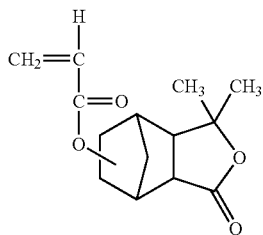

First, solution obtained by solving 5-norbornene-2,3-dicarboxylic acid anhydride of 34.47 grams into dry THF of 100 ml was dropped, while cooled with ices, into diethyl ether solution (3 mol/L) of methylmagnesiumbromide of 250 grams in argon atmosphere.

The resultant was stirred for two hours at room temperature, and then, 10% hydrochloric acid was added to the resultant to make the resultant acidic. Then, the resultant was stirred for an hour at 40 degrees centigrade. Then, diethyl ether of 200 ml was added to the resultant. Then, the resultant was washed with 3% aqueous solution of sodium carbonate and further brine in turn, and thereafter, was dried with magnesium sulfate.

After a solvent was removed, the residue was distilled under a reduced pressure (106–107 degrees centigrade/0.6 mmHg). Thus, there was obtained 3-oxo-4-oxa-5,5-dimethyltricyclo [5.2.1.0$^{2,6}$]-8-nonene of 20.12 grams.

Then, 3-oxo-4-oxa-5,5-dimethyltricyclo [5.2.1.0$^{2,6}$]-8-nonene of 20 grams was solved into dry THF of 50 ml, into which THF solution (1 mol/L) of $BH_3$ THF complex salt of 67 ml was dropped in argon atmosphere while cooled with ices.

The resultant was stirred for an hour while cooled with ices and further for an hour at room temperature, and then, water of 10 ml, NaOH aqueous solution (3 mol/L) of 22 ml, and 30% hydrogen peroxide solution of 15 ml were dropped in turn into the resultant.

Then, the resultant was stirred for two hours at room temperature. Then, diethyl ether of 200 ml was added to the resultant. Then, the diethyl ether organic layer was washed with saturated brine, and thereafter, was dried with magnesium sulfate. Then, a solvent was removed under a reduced pressure. Thus, there was quantitatively obtained alcohol.

Then, alcohol of 20 grams, N,N-dimethylaniline of 18.4 grams, and phenothiazine of 50 mg were solved into dry methylene chloride of 200 ml, and then, acryloil chloride of 10.96 grams were dropped into the resultant while cooled with ices.

After the resultant was stirred for four hours at room temperature, diethylether of 150 ml was added to the resultant. Then, the resultant was washed with 0.5N hydrochloric acid, 3% aqueous solution of sodium carbonate and further brine in turn, and thereafter, was dried with magnesium sulfate.

After a solvent was removed under a reduced pressure, the residue was purified in a silica-gel column (solvent for elution: hexane/ethyl acetate=2/1). Thus, there was obtained a target material, that is, acrylate by 10.2 grams in the form of transparent liquid. The yield was 40%.

The measurement results of $^1$H-NMR (reference sample: $CDCl_3$) of the obtained acrylate were as follows.

δ:
1.36(3H, s),
1.38(3H, m),
1.40–1.65(2H, m),
2.4–2.9(6H, m),
4.5–4.54(1H, m),
5.82(1H, dd),
6.09(1H, dd),
6.38(1H, d).

The measurement results of 1R (KBr disc) were as follows.

1R (KBr disc):
2968 cm$^{-1}$ [ν(C—H)],
1768 cm$^{-1}$, 1720 cm$^{-1}$ [ν(C=O)],
1636 cm$^{-1}$, 1618 cm$^{-1}$ [ν(C=C)],

Example 5

There was synthesized methacrylate having the structure indicated below, that is, methacrylate defined in accordance with the general formula (I) wherein $R^1$ represents a methyl group, $R^2$ and $R^3$ each represents a hydrogen atom, X represents —$CH_2$—, Z represents a hydrogen atom, and n is equal to one (1).

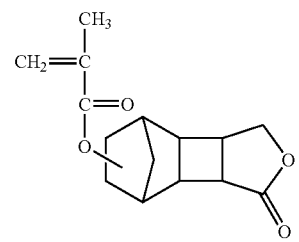

First, the monomer of 5 grams obtained in Example 1 and methacrylic acid of 4.2 grams were solved into dry toluene of 20 ml, and phosphotungstic acid•n-hydrates of 0.279 grams were added thereto.

Then, the resultant was stirred for three hours at 80 degrees centigrade. Then, diethyl ether of 100 ml was added to the resultant. Then, the resultant was washed with 3% aqueous solution of sodium carbonate and further brine in turn, and thereafter, was dried with magnesium sulfate.

After a solvent was removed, the residue was purified in a silica-gel column (solvent for elution: hexane/ethyl acetate=2/1). Thus, there was obtained a target material, that is, methacrylate by 1 gram. The yield was 13%.

The measurement results of 1R (KBr disc) for the obtained methacrylate were as follows.

1R (KBr disc):
2969 cm$^{-1}$ [ν(C—H)],
1765 cm$^{-1}$, 1722 cm$^{-1}$ [ν(C=O)],
1638 cm$^{-1}$ [ν(C=C)],

Example 6

There was synthesized acrylic polymer comprised of a structural unit by 30 mol % which is defined in accordance with the general formula (III) wherein $R^1$ represents a hydrogen atom, $R^2$ and $R^3$ each represents a methyl group, X represents —$CH_2$—, Z represents a hydrogen atom, and n is equal to one (1), a structural unit by 50 mol % which is defined in accordance with the general formula (VI-a) wherein $R^{11}$ represents a methyl group, and $R^{12}$ represents a 2-methyl-2-adamantyl group, and a structural unit by 20 mol % which is defined in accordance with the general formula (VI-a) wherein $R^{11}$ represents a methyl group, and $R^{12}$ represents a 3-hydroxy-1-adamantyl group.

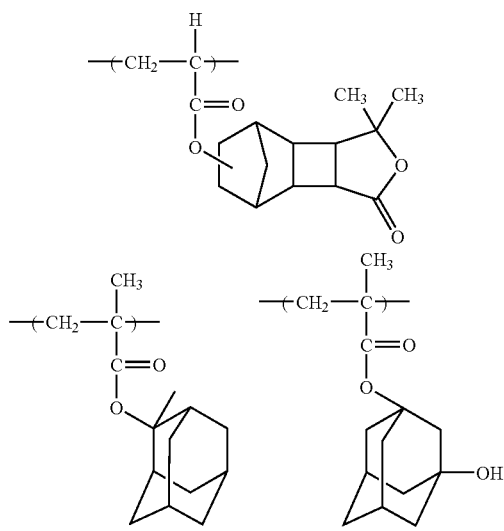

In a 100 ml-flask with a reflux tube, acrylate of 2 grams obtained in Example 3, 2-methyl-2-adamantylmethacrylate of 2.82 grams, and 3-hydroxyadamantylmethacrylate of 1.14 grams were solved in dry tetrahydrofuran of 40 ml. Further, AIBN of 158 mg (4 mol %) was added thereto.

Then, the resultant was stirred for four hours at 65–67 degrees centigrade in argon atmosphere, and then, naturally cooled. The resultant was poured into hexane of 400 ml, and the resultant precipitate was filtered.

Then, the resultant was reprecipitated and then purified. As a result, there was obtained a target material of 3.52 grams. The yield was 59%.

A copolymerization ratio of the obtained polymer was 30:50:20 (mol ratio), based on an integration ratio of $^1$H-NMR. Furthermore, a weight average molecular weight (Mw) and a degree of dispersion (Mw/Mn) of the obtained polymer were 9700 (equivalence in polystyrene) and 1.91, respectively, based on GPC analysis.

Example 7

There was synthesized a polymer in the same manner as Example 6 except that a monomer ratio, namely, acrylate obtained in Example 3: 2-methyl -2-adamantylmethacrylate: 3-hydroxyadamantylmethacrylate was set to be 0.15:0.55: 0.3 (mol ratio).

A copolymerization ratio of the obtained polymer was 0.15:0.54:0.31 (mol ratio), based on an integration ratio of $^1$H-NMR. Furthermore, a weight average molecular weight (Mw) of the obtained polymer was 8400.

Example 8

There was synthesized a polymer in the same manner as Example 6 except that a monomer ratio, namely, acrylate obtained in Example 3: 2-methyl -2-adamantylmethacrylate: 3-hydroxyadamantylmethacrylate was set to be 0.45:0.45: 0.1 (mol ratio).

A copolymerization ratio of the obtained polymer was 0.44:0.46:0.1 (mol ratio), based on an integration ratio of $^1$H-NMR. Furthermore, a weight average molecular weight (Mw) of the obtained polymer was 10500.

Example 9

There was synthesized a polymer in the same manner as Example 6 except that a content (concentration) of AIBN was set equal to 0.5 mol %.

A copolymerization ratio of the obtained polymer was 0.30:0.51:0.19 (mol ratio), based on an integration ratio of $^1$H-NMR. Furthermore, a weight average molecular weight (Mw) of the obtained polymer was 43000.

Example 10

There was synthesized a polymer in the same manner as Example 6 except that a content (concentration) of AIBN was set equal to 10 mol %.

A copolymerization ratio of the obtained polymer was 0.29:0.51:0.2 (mol ratio), based on an integration ratio of $^1$H-NMR. Furthermore, a weight average molecular weight (Mw) of the obtained polymer was 3900.

Example 11

There was synthesized acrylic polymer comprised of a structural unit by 30 mol % which is defined in accordance with the general formula (III) wherein $R^1$ represents a hydrogen atom, $R^2$ and $R^3$ each represents a methyl group, X represents —$CH_2$—, Z represents a hydrogen atom, and n is equal to one (1), a structural unit by 50 mol % which is defined in accordance with the general formula (VI-a) wherein $R^{11}$ represents a hydrogen atom, and $R^{12}$ represents a t-butoxycarbonyltetracyclododecyl group, and a structural unit by 20 mol % which is defined in accordance with the general formula (VI-a) wherein $R^{11}$ represents a methyl group, and $R^{12}$ represents a carboxytetracyclododecyl group.

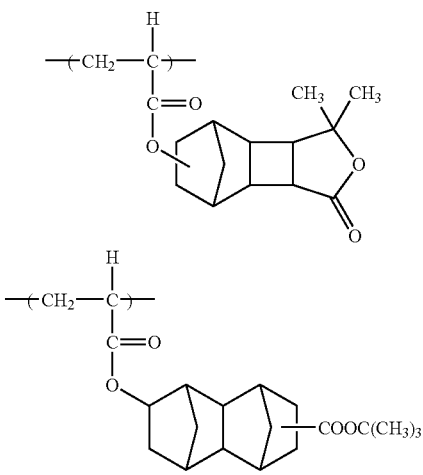

-continued

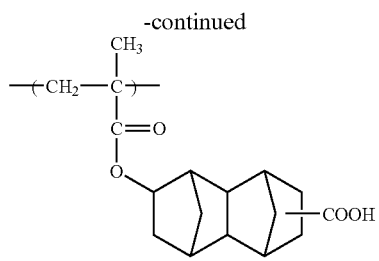

There was obtained the polymer by carrying out polymerization in the same manner as Example 6 except that t-butoxycarbonyltetracyclododecyl acrylate was employed in place of 2-methyl-2-adamantylmethacrylate, and carboxytetracyclododecylmethacrylate was employed in place of 3-hydroxy-1-adamantylmethacrylate. The yield was 54%.

A weight average molecular weight (Mw) and a degree of dispersion (Mw/Mn) of the obtained polymer were 10500 and 1.79, respectively, based on GPC analysis.

Example 12

There was synthesized acrylic polymer comprised of a structural unit by 30 mol % which is defined in accordance with the general formula (III) wherein $R^1$ represents a hydrogen atom, $R^2$ and $R^3$ each represents a methyl group, X represents —$CH_2$—, Z represents a hydrogen atom, and n is equal to one (1), a structural unit by 50 mol % which is defined in accordance with the general formula (VI-a) wherein $R^{11}$ represents a methyl group, and $R^{12}$ represents a 2-methyl-2-adamantyl group, and a structural unit by 20 mol % which is defined in accordance with the general formula (VI-a) wherein $R^{11}$ represents a hydrogen atom, and $R^{12}$ represents a 2,6-norbornanecarbolactone-5-yl group.

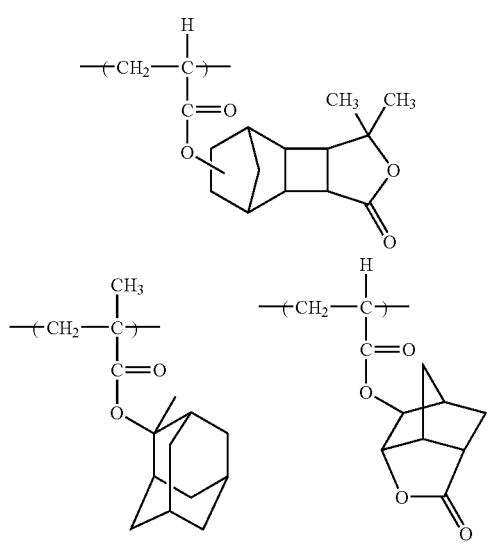

There was obtained the polymer by carrying out polymerization in the same manner as Example 6 except that 5-acryloiloxy-2,6-norbornanecarbolactone was employed in place of 3-hydroxy-1-adamantylmethacrylate. The yield was 51%.

A weight average molecular weight (Mw) and a degree of dispersion (Mw/Mn) of the obtained polymer were 9100 and 1.92, respectively, based on GPC analysis.

Example 13

There was synthesized acrylic polymer comprised of a structural unit by 30 mol % which is defined in accordance with the general formula (III) wherein $R^1$ represents a hydrogen atom, $R^2$ and $R^3$ each represents a methyl group, X represents —$CH_2$—, Z represents a hydrogen atom, and n is equal to zero (0), a structural unit by 50 mol % which is defined in accordance with the general formula (VI-a) wherein $R^{11}$ represents a methyl group, and $R^{12}$ represents a 2-methyl-2-adamantyl group, and a structural unit by 20 mol % which is defined in accordance with the general formula (VI-a) wherein $R^{11}$ represents a methyl group, and $R^{12}$ represents a 3-hydroxy-1-adamantyl group.

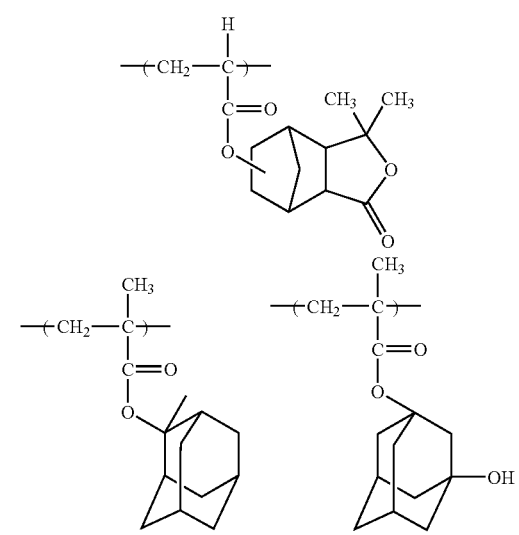

There was obtained the polymer by carrying out polymerization in the same manner as Example 6 except that acrylate obtained in Example 4 was employed in place of acrylate obtained in Example 3. The yield was 57%.

A weight average molecular weight (Mw) and a degree of dispersion (Mw/Mn) of the obtained polymer were 10400 and 1.88, respectively, based on GPC analysis.

Example 14

There was synthesized polymer comprised of a structural unit by 25 mol % which is defined in accordance with the general formula (IV) wherein $R^4$ and $R^5$ each represents a hydrogen atom, a structural unit by 25 mol % which is defined in accordance with the general formula (VI-d), and a structural unit by 50 mol % which is defined in accordance with the general formula (VI-a) wherein $R^{11}$ represents a methyl group, and $R^{12}$ represents a 2-methyl-2-adamantyl group.

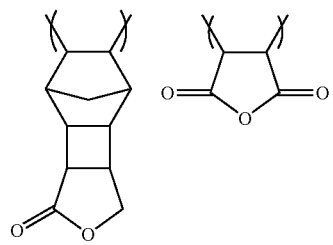

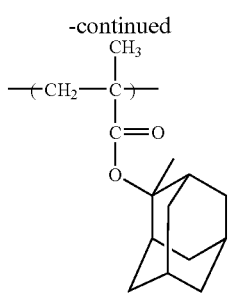

There was obtained the polymer by carrying out polymerization in the same manner as Example 6 except that monomer obtained in Example 1 was employed in place of monomer obtained in Example 3, and that maleic anhydride was employed in place of 3-hydroxy-1-adamantylmethacrylate. The yield was 31%.

A weight average molecular weight (Mw) and a degree of dispersion (Mw/Mn) of the obtained polymer were 8400 and 2.55, respectively, based on GPC analysis.

Example 15

There was synthesized polymer comprised of a structural unit by 50 mol % which is defined in accordance with the general formula (IV) wherein $R^4$ and $R^5$ each represents a methyl group, and a structural unit by 50 mol % which is defined in accordance with the general formula (VI-b) wherein $R^{13}$ represents a hydrogen atom, $R^{14}$ represents a t-butoxycarbonyl group, and $X^{11}$ and $X^{12}$ each represents a hydrogen atom, and $m^1$ is equal to zero (0).

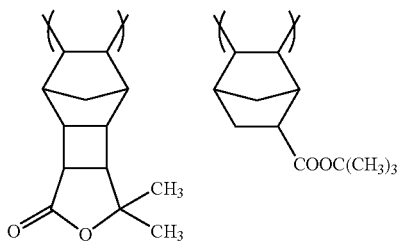

First, di-μ-chlorobis[(η-aryl) palladium (II)] of 0.101 grams and hexafluoroantimony acid silver of 0.191 grams were solved in methylene chloride of 30 ml. The solution was stirred for twenty minutes at room temperature, and thereafter, the resultant mixture was filtered.

Then, the filtrate was added to a mixture of the monomer of 2.84 grams obtained in Example 2, 5-norbornene-2-carboxylic acid t-butyl ester of 2.694 grams, and methylene chloride of 10 ml.

Then, the resultant was stirred for 24 hours at room temperature, and thereafter, was added to methanol of 400 ml to separate precipitated resin.

Then, the resultant resin was solved into methylene chloride of 40 ml. Then, methanol of 4 ml and sodium boron hydride of 0.4 grams were added to the resultant solution.

The solution was stirred for three hours at room temperature, and was left for 24 hours at room temperature. Thereafter, precipitated particles of Pd(0) were filtered out, and the filtrate was poured into methanol of 400 ml to separate precipitated resin. Thus, there was obtained a target material of 1.77 grams. The yield was 30%.

A weight average molecular weight (Mw) and a degree of dispersion (Mw/Mn) of the obtained polymer were 14000 and 2.44, respectively, based on GPC analysis.

Example 16

There was synthesized acrylic polymer comprised of a structural unit by 100 mol % which is defined in accordance with the general formula (III) wherein $R^1$ represents a hydrogen atom, $R^2$ and $R^3$ each represents a methyl group, X represents —$CH_2$—, Z represents a hydrogen atom, and n is equal to one (1).

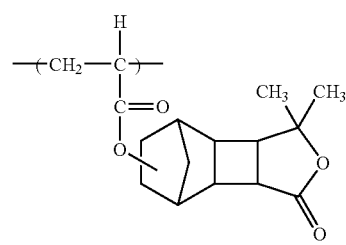

Acrylate of 0.6 grams obtained in Example 3 was solved in dry THF of 3 ml. Further, AIBN of 0.0143 g was added thereto.

Then, the resultant was stirred for four hours at 65–67 degrees centigrade in argon atmosphere, and then, naturally cooled. The resultant mixture was poured into hexane of 50 ml, and the resultant precipitate was filtered.

Then, the resultant was reprecipitated and then purified. As a result, there was obtained a target material of 0.44 grams. The yield was 73%.

A weight average molecular weight (Mw) and a degree of dispersion (Mw/Mn) of the obtained polymer were 11200 and 2.12, respectively, based on GPC analysis.

[Estimate of Resistance to Etching]

Acrylic polymer of 2 grams obtained in Example 6 was solved into propyleneglycolmonomethyletheracetate of 10 grams, and was filtered with a Teflon filter of 0.2 micrometers.

Then, the filtrate was coated onto a 3-inch silicon substrate by a spin-coating process. Then, the substrate was baked on a hot plate for 60 seconds at 90 degrees centigrade. Thus, there was formed a thin film having a thickness of 0.7 micrometers.

The film was etched by means of a reactive ion etching (RIE) apparatus available from Nichiden Anelva as the model DEM 451. Then, an etching rate to $CF_4$ gas was measured Etching conditions were as follows.
Power: 100 W
Pressure: 5 Pa
Gas flow rate: 30 sccm Etching rates were measured in the same way with respect to acrylic polymer obtained in Example 11 and norbornane polymer obtained in Example 15.

As reference samples, etching rates were measured in the same way with respect to commercially available novolak resist, poly(p-vinylphenol) used as base resin for KrF resist, and poly(methylmethacrylate) which is a resin having no bridged alicyclic hydrocarbon radical in its molecular structure.

The measurement results are shown in Table 1. The etching rates are standardized with respect to novolak resist.

TABLE 1

| | Etching rate (Relative ratio) |
|---|---|
| Example 6 | 1.02 |
| Example 11 | 1.02 |
| Example 15 | 0.98 |
| Poly(methylmethacrylate) | 1.9 |
| Poly(p-vinylphenol) | 1.2 |
| Novolak resist | 1 |

It was proved that the polymer (Examples 6, 11 and 15) in accordance with the present invention had a higher etching rate to $CF_4$ gas and higher resistance to dry etching than the resins listed as reference samples.

[Estimate to Transparency]

Acrylic polymer of 1.8 grams obtained in Example 6 was solved into propyleneglycolmonomethyletheracetate of 10 grams, and was filtered with a Teflon filter of 0.2 micrometers.

Then, the filtrate was coated onto a 3-inch quartz substrate by a spin-coating process. Then, the substrate was baked on a hot plate for 60 seconds at 90 degrees centigrade. Thus, there was formed a thin film having a thickness of 0.4 micrometers.

Then, transmittance of the thin film was measured by means of a spectrophotometer for ultraviolet and visible region, with respect to 193.4 nm as a primary wavelength of ArF excimer laser beams.

Further, transmittances of acrylic polymer obtained in Example 11 and norbornane polymer obtained in Example 15 were measured in the same way.

The measurement results were shown in Table 2.

TABLE 2

| | Transmittance at a wavelength of 193.4 nm |
|---|---|
| Example 6 | 81% |
| Example 11 | 80% |
| Example 15 | 69% |

It was proved that the polymer (Examples 6, 11 and 15) in accordance with the present invention had transparency sufficient to compose a single-layer resist of the polymer.

[Estimate to Patterning]

A mixture of acrylic polymer of 2 grams obtained in Example 6, photo acid generator (triphenylsulfoniumnonaphlate) of 0.04 grams, 2,6-diisopropylaniline of 0.004 grams, and propyleneglycolmonomethyletheracetate of 11.5 grams was filtered with a 0.2-μm Teflon filter to thereby prepare resist composition.

An organic antireflection film having a thickness of 0.1 micrometer was formed on a 8-inch silicon substrate. The above-mentioned resist composition was coated onto the substrate by a spin-coating process, and then, was baked on a hot plate for a minute at 130 degrees centigrade. Thus, there was formed a thin resist film having a thickness of 0.4 micrometers.

Then, the resist film was exposed to light by means of an ArF stepper apparatus (available from Nikon, NA=0.6).

Immediately after the exposure, the resist film was baked on a hot plate for 60 seconds at 135 degrees centigrade. Then, the resist film was emerged in aqueous solution of 2.38% $(CH_3)_4NOH(TMAH)$ for 60 seconds at a liquid temperature of 23 degrees centigrade for development. Then, the resist film was rinsed with pure water for 60 seconds.

As a result, only a portion of the resist film having been exposed to light was removed by the developing agent, and thus, there was obtained a positive pattern. A resolution was measured by SEM observation with respect to the obtained pattern. Sensitivity was determined as a light volume at which the obtained L/S (line and space) pattern could be resolved at 1:1.

Patterning was estimated in the same way as mentioned above with respect to resist composition composed of acrylic polymer obtained in Example 11 and resist composition composed of norbornane polymer obtained in Example 15.

The estimate results are shown in Table 3.

TABLE 3

| | Resolution (μmL/S) | Density (mJ/cm$^2$) |
|---|---|---|
| Resist including resin of Example 6 | 0.13 | 21 |
| Resist including resin of Example 11 | 0.13 | 18 |
| Resist including resin of Example 15 | 0.15 | 28 |

It was proved that a photoresist material including the polymer in accordance with the present invention (Examples 6, 11 and 15) had high sensitivity and resolution.

[Estimate to Adhesion to a Substrate]

A substrate on which a photoresist was patterned was observed by means of SEM. As a result, it was observed that the pattern was not peeled off the substrate, and hence, it was found out that a photoresist material including the polymer in accordance with the present invention (Examples 6, 11 and 15) had sufficient adhesion to a substrate.

Example 17

Monomer obtained in Example 3 was polymerized in ring opening metathesis. Hydrogen was added to the resultant resin through palladium catalyst. Thus, there was obtained acrylic polymer comprised of a structural unit by 100 mol % which is defined in accordance with the general formula (III) wherein $R^1$ represents a hydrogen atom, $R^2$ and $R^3$ each represents a methyl group, X represents —$CH_2$—, Z represents a hydrogen atom, and n is equal to one (1).

Example 18

Resist composed of polymer obtained in Examples 7 to 10 and 12 to 14 has sufficient resistance to etching, transparency, sensitivity, resolution and adhesion to a substrate.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The entire disclosure of Japanese Patent Application No. 2002-190827 filed on Jun. 28, 2002 including specification, claims, drawings and summary is incorporated herein by reference in its entirety.

What is claimed is:

1. An unsaturated monomer having a bridged alicyclic γ-lactone structure defined in formula (II):

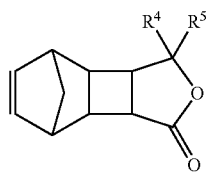

(II)

wherein $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

2. A polymer resulted from (co)polymerizing a monomer composition containing at least one of (metha)acrylate derivative and unsaturated monomer, wherein said (metha)acrylate derivative has a bridged alicyclic γ-lactone structure defined in formula (I):

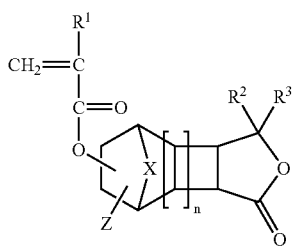

(I)

wherein $R^1$ represents one of a hydrogen atom and a methyl group, $R^2$ and $R^3$ each represents one of a hydrogen atom and an alkyl group having a carbon number in the range of 1 to 6 both inclusive, or $R^2$ and $R^3$ link each other, and each represents an alkylene group having a carbon number in the range of 1 to 6 both inclusive and cooperating with a carbon atom to which $R^2$ and $R^3$ link to define a ring, X represents one of —CH2— and —O—, Z represents one of a hydrogen atom and a methyl group, and n represents one of 0 and 1 wherein when n represents 0 and X represents —CH2—, $R^2$ and $R^3$ each represents a carbon number in the range of 1 to 6 both inclusive, said unsaturated monomer has a bridged alicyclic γ-lactone structure defined in formula (II):

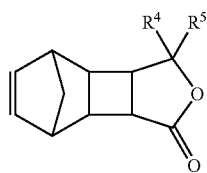

(II)

wherein $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

3. The polymer as set forth in claim 2, wherein a weight-average molecular weight of said polymer is in the range of 2,000 to 200,000 both inclusive.

4. A chemically-amplified resist composition containing a polymer, wherein said polymer is resulted from (co)polymerizing a monomer composition containing at least one of (metha)acrylate derivative and unsaturated monomer, wherein said (metha)acrylate derivative has a bridged alicyclic γ-lactone structure defined in formula (I):

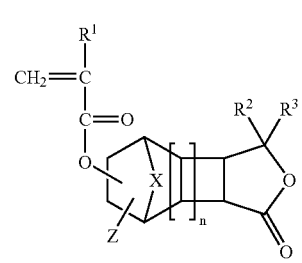

(I)

wherein $R^1$ represents one of a hydrogen atom and a methyl group, $R^2$ and $R^3$ each represents one of a hydrogen atom and an alkyl group having a carbon number in the range of 1 to 6 both inclusive, or $R^2$ and $R^3$ link each other, and each represents an alkylene group having a carbon number in the range of 1 to 6 both inclusive and cooperating with a carbon atom to which $R^2$ and $R^3$ link to define a ring, X represents one of —CH2— and —O—, Z represents one of a hydrogen atom and a methyl group, and n represents one of 0 and 1 wherein when n represents 0 and X represents —CH2—, $R^2$ and $R^3$ each represents a carbon number in the range of 1 to 6 both inclusive, said unsaturated monomer has a bridged alicyclic γ-lactone structure defined in formula (II):

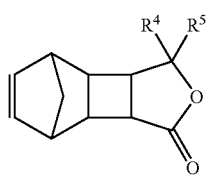

(II)

wherein $R^4$ and $R^5$ each represents one of a hydrogen atom and an alkyl group having a carbon number in the range of 1 to 6 both inclusive, or $R^4$ and $R^5$ link each other, and each represents an alkylene group having a carbon number in the range of 1 to 6 both inclusive and cooperating with a carbon atom to which $R^4$ and $R^5$ link to define a ring.

5. The chemically-amplified resist composition as set forth in claim 4, further comprising a photo acid generator which generates acid when exposed to light.

6. The chemically-amplified resist composition as set forth in claim 5, wherein a content of said photo acid generator is in the range of 0.2 to 30 mass % both inclusive relative to a total content of said polymer and said photo acid generator.

7. The chemically-amplified resist composition as set forth in claim 5, wherein said photo acid generator generates acid when light having a wavelength in the range of 180 to 220 nanometers both inclusive is irradiated thereto.

8. A method of forming a pattern, comprising at least the steps, in sequence, of:

coating a chemically-amplified resist composition defined in claim 4 onto a substrate;

baking said chemically-amplified resist composition;

exposing said chemically-amplified resist composition to light having a wavelength in the range of 180 to 220 nanometers both inclusive;

baking said chemically-amplified resist composition; and developing said chemically-amplified resist composition.

9. The method as set forth in claim 8, wherein said light is comprised of ArF excimer laser beams.

* * * * *